US012797592B2

(12) United States Patent
Silverstein et al.

(10) Patent No.: US 12,797,592 B2
(45) Date of Patent: Nov. 17, 2026

(54) VAGINAL DILATOR ASSEMBLY

(71) Applicant: Soul Source Therapeutic Devices, Inc., North Hollywood, CA (US)

(72) Inventors: Jeff Silverstein, North Hollywood, CA (US); Lloyd Silverstein, North Hollywood, CA (US)

(73) Assignee: Soul Source Therapeutic Devices, Inc., North Hollywood, CA (US)

( * ) Notice: Subject to any disclaimer, the term of this patent is extended or adjusted under 35 U.S.C. 154(b) by 31 days.

(21) Appl. No.: 19/063,652

(22) Filed: Feb. 26, 2025

(65) Prior Publication Data

US 2026/0249059 A1 Aug. 27, 2026

(51) Int. Cl.
*A61M 29/00* (2006.01)

(52) U.S. Cl.
CPC ..... *A61M 29/00* (2013.01); *A61M 2205/0216* (2013.01); *A61M 2205/05* (2013.01); *A61M 2210/1475* (2013.01)

(58) Field of Classification Search
CPC .......... A61M 29/00; A61M 2205/0216; A61M 2205/05; A61M 2210/1475
See application file for complete search history.

(56) References Cited

U.S. PATENT DOCUMENTS 6,058,932 A * 5/2000 Hughes ............. A61M 16/0006 482/13
10,130,799 B2 * 11/2018 Kesten .................. A61B 17/24

OTHER PUBLICATIONS

Soul Source GRS Vaginal Trainers—Intermediate Set—https://www.soulsource.com/collections/grs-vaginal-trainers/products/soul-source-grs-vaginal-trainers-intermediate-set.

* cited by examiner

*Primary Examiner* — Vi X Nguyen
(74) *Attorney, Agent, or Firm* — Jeffer Mangels & Mitchell LLP; Brennan C. Swain, Esq.

(57) ABSTRACT

A vaginal dilator assembly that includes a cylindrical main body portion and a rod disposed in a lumen defined in the main body portion. The main body portion includes an axial portion and an offset portion. The main body portion includes a top surface, a bottom surface, a first side surface, a second side surface, a proximal end and a distal end. The lumen extends from the axial portion to the offset portion. The axial portion defines a first axis and the offset portion defines a second axis and the second axis is not co-axial with the first axis. A rod is disposed in the lumen. The rod comprises a material that is more rigid than a material of the main body portion.

15 Claims, 5 Drawing Sheets

VAGINAL DILATOR ASSEMBLY

FIELD OF THE INVENTION

The present invention relates to vaginal dilators or trainers and more specifically relates to a vaginal dilator assembly that includes a main body portion and an internal rod.

BACKGROUND OF THE INVENTION

Vaginal dilators or trainers may be used for multiple purposes, including after vaginoplasty. For example vaginal dilators may be used by women, such as transgender women, post-vaginoplasty surgery. In particular, transgender women may have a male pelvic bone that may get in the way during use of vaginal dilators. The pelvic bone may be an issue for cisgender women as well.

The background description disclosed anywhere in this patent application includes information that may be useful in understanding the present invention. It is not an admission that any of the information provided herein is prior art or relevant to the presently claimed invention, or that any publication specifically or implicitly referenced is prior art.

SUMMARY OF THE PREFERRED EMBODIMENTS

In accordance with a first aspect of the present invention there is provided a vaginal dilator assembly that includes a cylindrical main body portion and a rod disposed in a lumen defined in the main body portion. The main body portion includes an axial portion and an offset portion. The main body portion includes a top surface, a bottom surface, a first side surface, a second side surface, a proximal end and a distal end. The lumen extends from the axial portion to the offset portion. The axial portion defines a first axis and the offset portion defines a second axis and the second axis is not co-axial with the first axis. A rod is disposed in the lumen. The rod comprises a material that is more rigid than a material of the main body portion. In a preferred embodiment, a vibration recess having a vibration surface is defined in the proximal end of the main body portion, such that a vibration device can be placed into the vibration recess and against the vibration surface to transmit vibrations through the vaginal dilator assembly. The rod is configured to transmit the vibrations from the proximal end of the main body portion to the distal end of the main body portion.

The vaginal dilator assembly may include a series of depth indicating numbers arranged axially along the top surface of the main body portion. The main body portion may include an offset end portion defined between the distal end of the main body portion and the rod.

In accordance with another aspect of the present invention, there is provided a method of using a vaginal dilator assembly. The method includes the steps of obtaining the vaginal dilator assembly, obtaining a vibration device having a convex portion, inserting the vaginal dilator assembly into a vaginal canal, placing the convex portion of the vibration device in the vibration recess and against the vibration surface, and transmitting vibrations through the vaginal dilator assembly and to the vaginal canal.

The dilator or vaginal dilator assembly may include a curve or a non-axial portion at the distal end thereof to avoid the pelvic bone, as discussed in the background section. However, the curve or non-axial portion may make it difficult to manufacture the dilators. The present invention may include an outside portion or main body portion that is manufactured from a silicone or similar soft material (any polymer is within the scope of the present invention with a nylon (or other more rigid material) internal rod or the like on the inside thereof. The rod may be made of any polymer or polyimide material, provided the material of the rod is more rigid or stiffer than the material of the main body portion. This construction allows the dilator to have some flexibility or "give" and is not as rigid as the prior art. It will be appreciated that the silicone construction of the outer or main body portion may not provide enough rigidity for the dilator to work properly (e.g., if the entire dilator was made of silicone. The rigid internal rod helps with this issue. In a preferred embodiment, the internal rod does not extend all the way to the distal end of the dilator assembly (or the main body portion), thus allowing the curved or non-axial portion to flex for purposes of avoiding the pelvic bone. Another advantage over the prior art of using silicone for the main body portion is the ability for users to autoclave the dilator assemblies for sterilization purposes. In an exemplary manufacturing process, first, the rod is created via a mold process. Next, the rod is placed in the shaped grooves in the two halves that form the lumen of the main body portion for final molding (to form the main body portion in one piece around the rod). After the dilator assembly is removed from the mold, it is baked and sanded and may then have the indicators and/or other wording or indicia printed thereon.

Each dilator or dilator assembly may be part of a set of dilators (e.g., six dilators or dilator assemblies in a set) that allow the training of the vaginal canal over time as larger diameter dilators within the set are used. During use, at least one dilator assembly within the set is used daily after surgery or other event that results in the use of a set of dilator assemblies (e.g., surgery, cancer treatment, etc.). In a preferred embodiment, each dilator assembly includes a series of depth indicators thereon, which may be a dot or circle or other indicator that indicates to the user the depth at which the dilator assembly is inserted into the vaginal canal. The indicators may also be numbers or letters. For example, the dilator assembly may include five numbered indicators (e.g., 1-5). In another embodiment, the dilator assembly may include more than five or less than five indicators (e.g., anywhere between one and ten indicators is within the scope of the invention). The indicator numbering system may allow the user to communicate better with their doctor when discussing how far they are able to insert the dilator assembly. The indicators may be a predetermined distance from one another or from either end of the main body portion. For example, the numbers may be approximately 12 mm from the center of one indicator number to the next. The dilator assembly may also include one or more finger grooves or recesses or the like that may aid during use. For example, the dilator assembly may include one finger groove on the top surface (e.g., for the thumb) and three finger grooves on the bottom surface of the dilator assembly.

In a preferred embodiment, the proximal end of the dilator assembly may include a concavity, indentation or recess defined therein, which may be referred to herein as a vibration recess. This vibration recess may be used to mate or dock with a vibration device. The vibration device may include a convex shaped portion that is inserted into or mated with the vibration recess. When the vibration device is activated, vibrations are transmitted through the internal rod (which may be referred to herein as a vibration transmission member or rod) and the main body portion and to the wall of the vaginal canal. These vibrations may help the user with blood flow, scar tissue, healing and the like and may help open or increase the diameter of the vaginal canal during treatment. The vibration recess may also aid in gripping or using the dilator assembly. Often after vaginoplasty, the neo-vagina may try to push or force the dilator out of the vagina. The vibration recess may serve as a location for the user to rest their thumb or finger to help hold the dilator assembly at the desired depth.

DETAILED DESCRIPTION OF THE PREFERRED EMBODIMENTS

Figure 1:
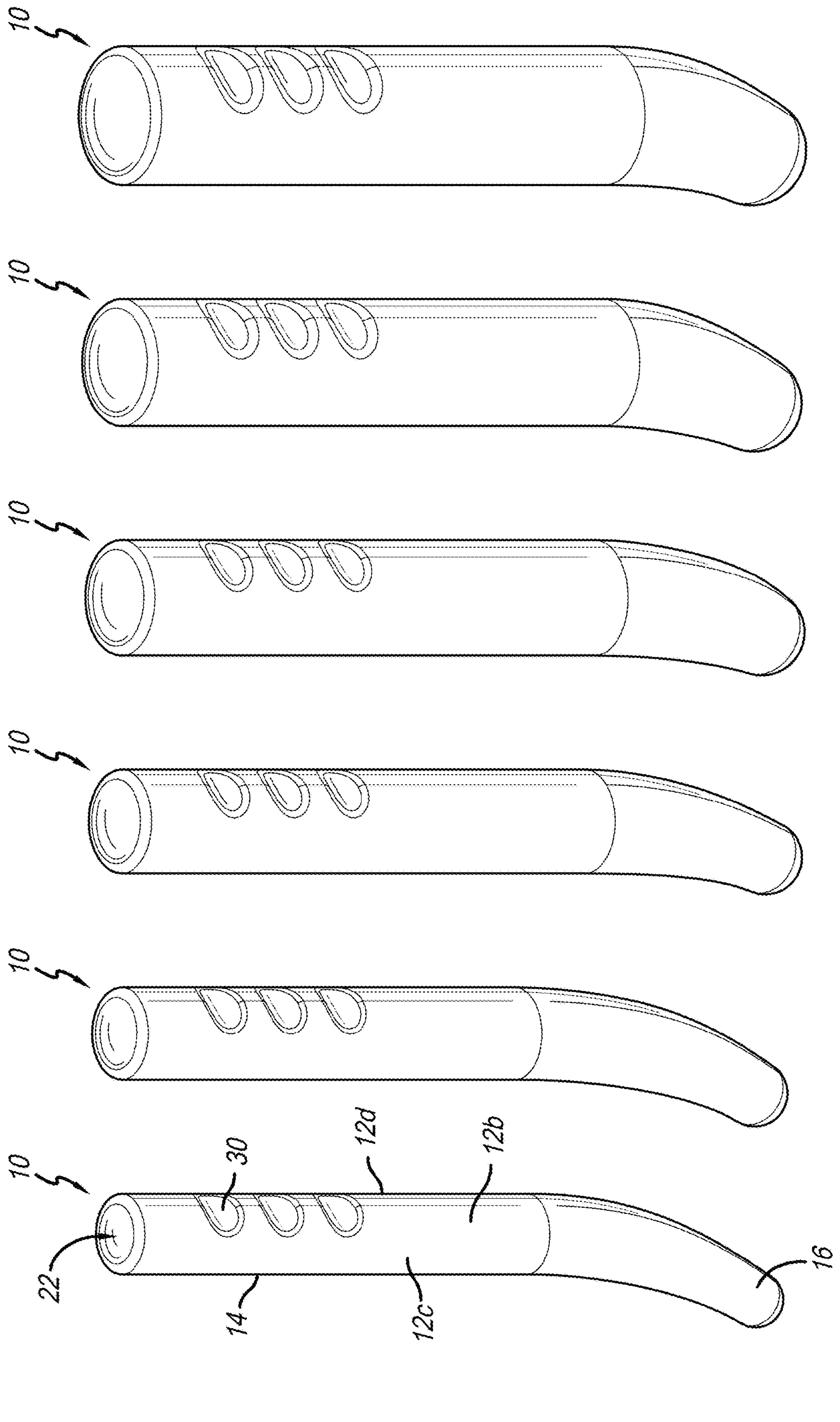
FIG. 1 is a perspective view of a plurality of vaginal dilator assemblies in accordance with a preferred embodiment of the present invention.
Figure 2:
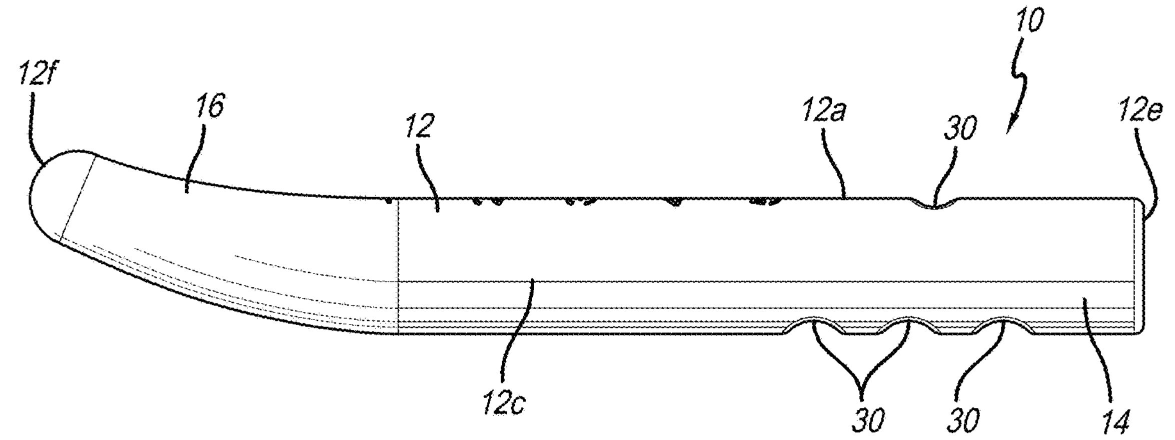
FIG. 2 is a side elevational view of a vaginal dilator assembly in accordance with a preferred embodiment of the present invention.

The following description and drawings are illustrative and are not to be construed as limiting. Numerous specific details are described to provide a thorough understanding of the disclosure. However, in certain instances, well-known or conventional details are not described in order to avoid obscuring the description. References to one or an embodiment in the present disclosure can be, but not necessarily are references to the same embodiment; and, such references mean at least one of the embodiments. If a component is not shown in a drawing then this provides support for a negative limitation in the claims stating that that component is "not" present. However, the above statement is not limiting and in another embodiment, the missing component can be included in a claimed embodiment.

Reference in this specification to "one embodiment," "an embodiment," "a preferred embodiment" or any other phrase mentioning the word "embodiment" means that a particular feature, structure, or characteristic described in connection with the embodiment is included in at least one embodiment of the disclosure and also means that any particular feature, structure, or characteristic described in connection with one embodiment can be included in any embodiment or can be omitted or excluded from any embodiment. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others and may be omitted from any embodiment. Furthermore, any particular feature, structure, or characteristic described herein may be optional. Similarly, various requirements are described which may be requirements for some embodiments but not other embodiments. Where appropriate any of the features discussed herein in relation to one aspect or embodiment of the invention may be applied to another aspect or embodiment of the invention. Similarly, where appropriate any of the features discussed herein in relation to one aspect or embodiment of the invention may be optional with respect to and/or omitted from that aspect or embodiment of the invention or any other aspect or embodiment of the invention discussed or disclosed herein.

The terms used in this specification generally have their ordinary meanings in the art, within the context of the disclosure, and in the specific context where each term is used. Certain terms that are used to describe the disclosure are discussed below, or elsewhere in the specification, to provide additional guidance to the practitioner regarding the description of the disclosure. For convenience, certain terms may be highlighted, for example using italics and/or quotation marks: The use of highlighting has no influence on the scope and meaning of a term; the scope and meaning of a term is the same, in the same context, whether or not it is highlighted.

It will be appreciated that the same thing can be said in more than one way. Consequently, alternative language and synonyms may be used for any one or more of the terms discussed herein. No special significance is to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and is not intended to further limit the scope and meaning of the disclosure or of any exemplified term. Likewise, the disclosure is not limited to various embodiments given in this specification.

Without intent to further limit the scope of the disclosure, examples of instruments, apparatus, methods and their related results according to the embodiments of the present disclosure are given below. Note that titles or subtitles may be used in the examples for convenience of a reader, which in no way should limit the scope of the disclosure. Unless otherwise defined, all technical and scientific terms used herein have the same meaning as commonly understood by one of ordinary skill in the art to which this disclosure pertains. In the case of conflict, the present document, including definitions, will control.

It will be appreciated that terms such as "front," "back," "top," "bottom," "side," "short," "long," "up," "down," "aft," "forward," "inboard," "outboard" and "below" used herein are merely for ease of description and refer to the orientation of the components as shown in the figures. It should be understood that any orientation of the components described herein is within the scope of the present invention.

Referring now to the drawings, wherein the showings are for purposes of illustrating the present invention and not for purposes of limiting the same, the drawings show one or more vaginal dilator assemblies 10. FIG. 1 shows a series of vaginal dilator assemblies 10 that are each a different sizes and/or diameters. It will be appreciated that during the course of treatment, different diameter vaginal dilator assemblies may be used. FIGS. 2-6 show a single vaginal dilator assembly 10 and the components thereof in a preferred embodiment of the present invention.

As shown in FIGS. 1-4, in a preferred embodiment, the vaginal dilator assembly 10 includes a cylindrical main body portion 12 that includes an axial portion 14, an offset portion 16 and a lumen 18 defined therein. The main body portion 12 includes a top surface **12*a*, a bottom surface 12*b*, a first side surface 12*c*, a second side surface 12*d*, a proximal end 12*e* and a distal end 12*f*. The lumen preferably extends from the axial portion 14 to the offset portion 16. However, this is not a limitation on the present invention, and the lumen may be present in only one of the axial portion 14 or the offset portion 16. It will be appreciated that the main body portion 12 is generally cylindrical or round (or other shape) and that the portion of the circumference or outer surface of the main body portion that is considered the top, bottom and first and second sides may be relative. However, these designations are provided based on the orientation in at least some of the figures (e.g., FIG. 2**). Furthermore, the four sides or top, bottom and first and second sides may be approximately a 90 degree portion of the circumference of the outer surface of the main body portion.

Figure 3:
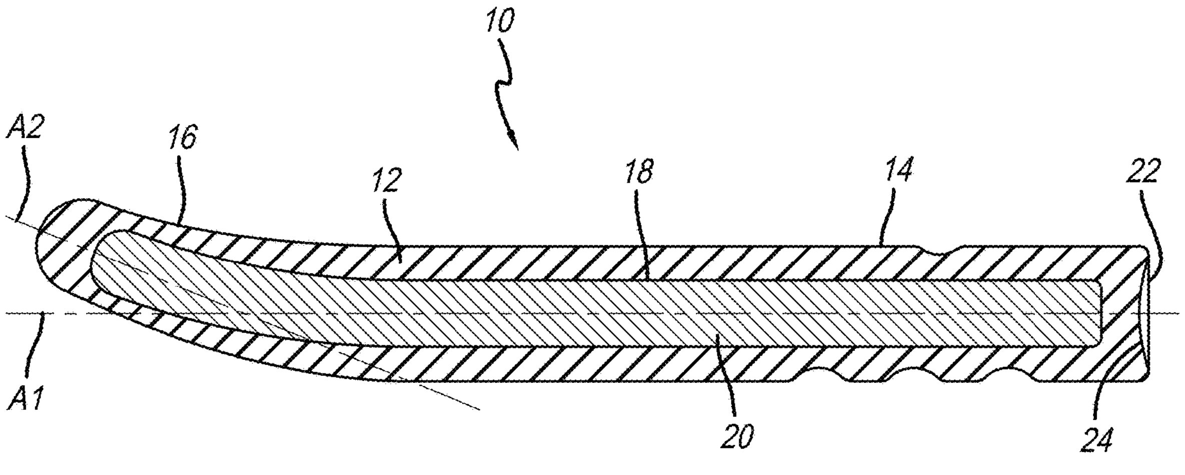
FIG. 3 is a cross-sectional view of the vaginal dilator assembly if FIG. 2.
Figure 4:
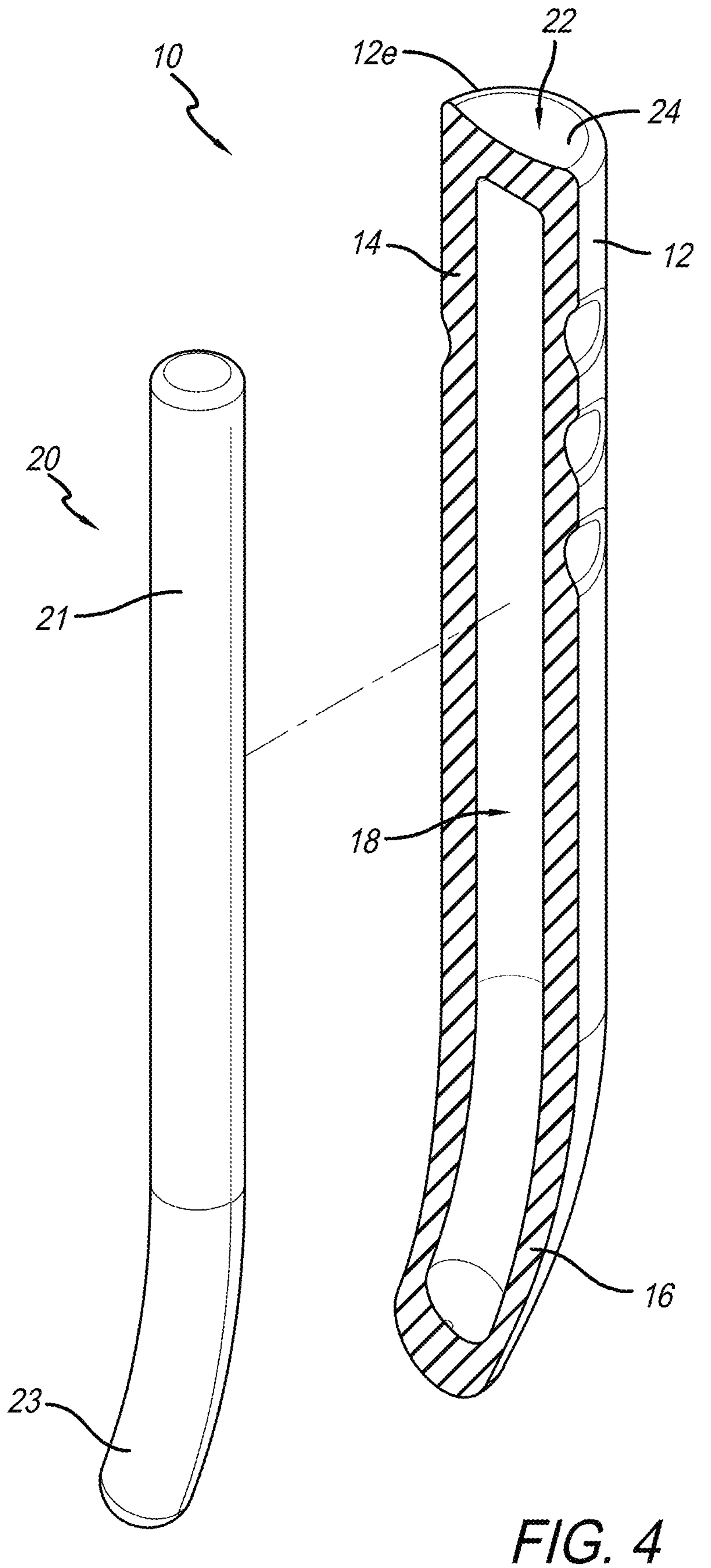
FIG. 4 is a cross-sectional perspective view of the vaginal dilator assembly shown in FIG. 2, with the rod exploded from the lumen.

As is best shown in FIG. 3, the axial portion 14 defines a first axis A1 and the offset portion 16 defines a second axis A2. In a preferred embodiment, the second axis A2 is not co-axial with the first axis A1. In another embodiment the offset portion may be omitted and the entire vaginal dilator assembly may be straight or include a single axis. The offset portion may be curved or straight. In a preferred embodiment, a rod 20 is disposed in the lumen 18. The rod 20 may comprise a material that is more rigid than the material of the main body portion 12. For example, the main body portion 12 may comprise silicone and the rod 20 may comprise nylon. As shown in FIG. 4, the rod 20 includes an axial portion 21 and an offset portion 23. As shown in FIG. 3, the lumen 18 is enclosed within the main body portion 12. In another embodiment, the lumen 18 may be open to one or both of the proximal and distal ends of the main body portion 12 (e.g., the main body portion may be tubular).

Figure 5:
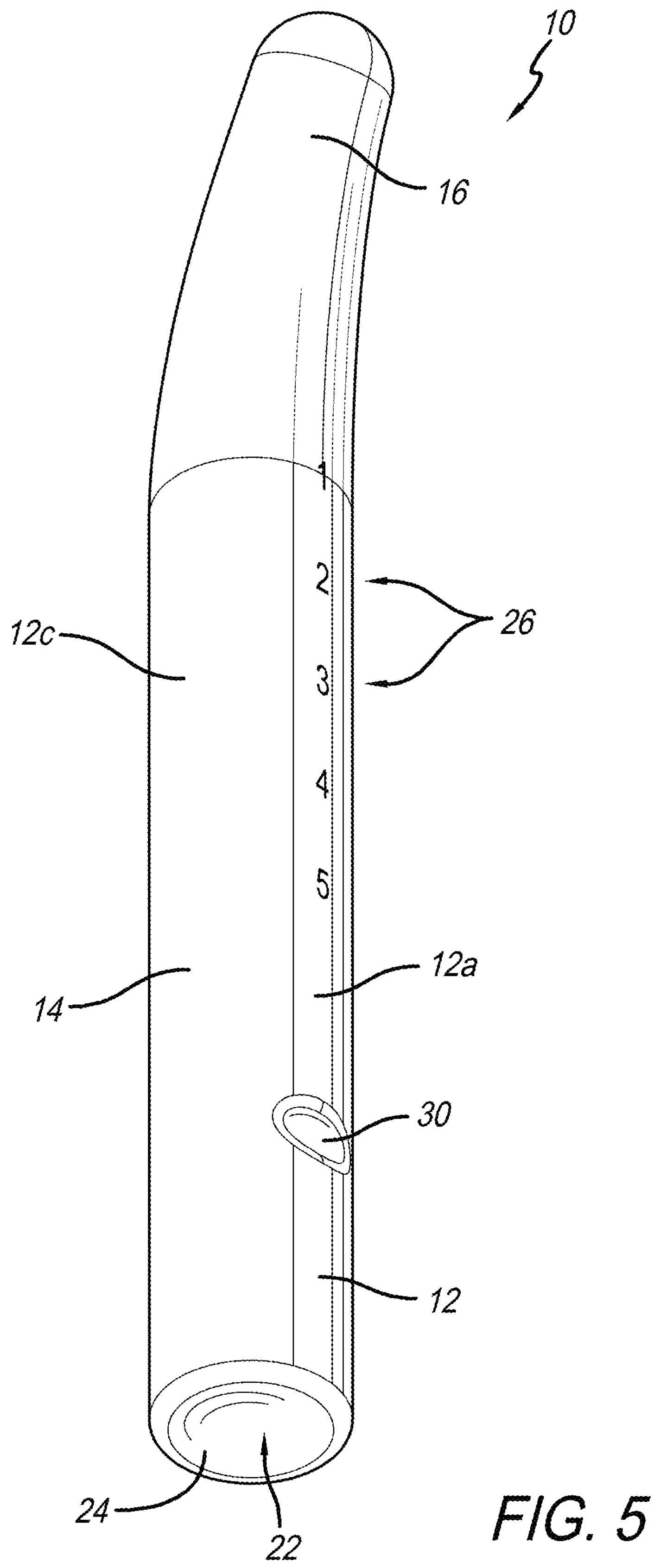
FIG. 5 is perspective view of the vaginal dilator of FIG. 2.
Figure 6:
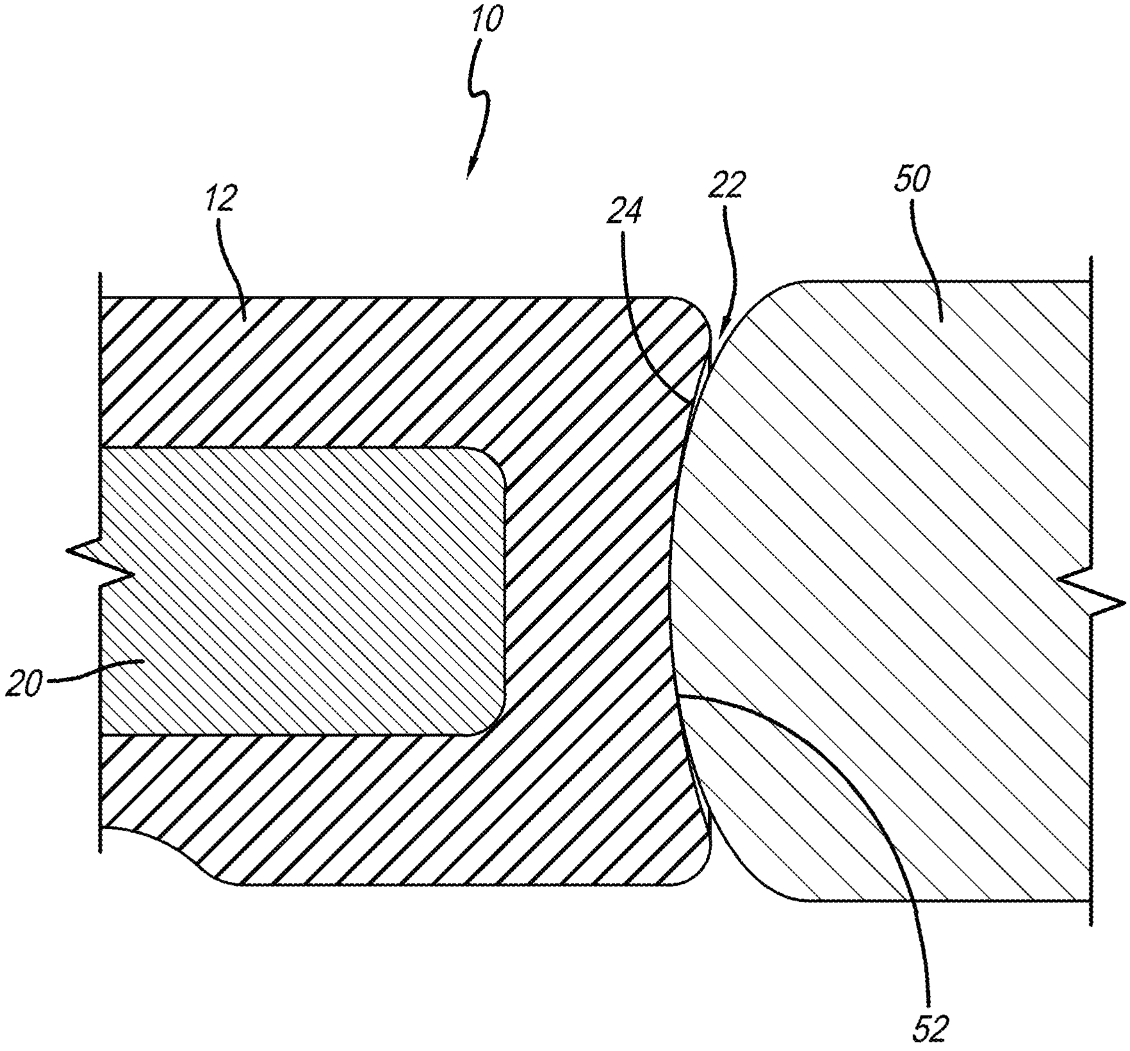
FIG. 6 is a detail cross-section of the proximal end of the vaginal dilator assembly with a vibration device received in the vibration recess.

As shown in FIGS. 5 and 6, in a preferred embodiment, the vaginal dilator assembly 10 includes a vibration recess 22 having a vibration surface 24 defined in the proximal end 12*e* of the main body portion 12. In use, a vibration device 50 can be placed into the vibration recess 22 and against the vibration surface 24 to transmit vibrations through the vaginal dilator assembly 10. The vibration device 50 may include a convex shaped portion 52 that is mated with or docked in the vibration recess 22, as shown in FIG. 6. In a preferred embodiment, the rod 20 transmits the vibrations from the proximal end 12*e* of the main body portion 12 to the distal end 12*f* of the main body portion. The harder or more rigid material of the rod 20 helps transmit the vibrations throughout the vaginal dilator assembly 10 and the main body portion 12 thereof. In an embodiment where the lumen 18 is open to the proximal end 12*e* of the main body portion 12, the vibration device 50 may be placed directly against the proximal end of the rod. The rod may include the vibration recess and vibration surface.

In a preferred embodiment, the rod 20 does not extend all the way to the distal end 12*f* of the main body portion 12, thus defining an offset end portion 28 in the main body portion 12 between the rod 20 and the distal end 12*f*. Because the offset end portion 28 is made of a softer material (e.g., silicone) than the rod 20, the offset end portion 28 may flex during use for purposes of avoiding the pelvic bone. The rigid rod 20 allows easy insertion of the vaginal dilator assembly 10 and the softer offset end portion 28 is flexible for comfort and flexibility.

As shown in FIG. 5, in a preferred embodiment, the vaginal dilator assembly 10 includes a series of depth indicating numbers 26 arranged axially along the main body portion 12. In a preferred embodiment, the depth indicating numbers 26 are disposed on the top surface 12*a* of the main body portion 12. Preferably, the depth indicating numbers 26 are printed on the outside surface of the main body portion as opposed to being molded into the material or raised so that the depth indicating numbers 26 don't cause issues during insertion. In another embodiment, the depth indicating numbers can be molded into the material or otherwise secured to the outside surface of the main body portion.

As shown in the figures, in a preferred embodiment, the vaginal dilator assembly 10 includes at least one finger recess 30 defined in the top surface 12*a* of the main body portion and one or more and preferably three finger recesses 30 defined in the bottom surface 12*b* of the main body portion. Any number of finger recesses positioned anywhere on the main body portion is within the scope of the present invention.

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof, means any connection or coupling, either direct or indirect, between two or more elements; the coupling of connection between the elements can be physical, logical, or a combination thereof. Additionally, the words "herein," "above," "below," and words of similar import, when used in this application, shall refer to this application as a whole and not to any particular portions of this application. Where the context permits, words in the above Detailed Description of the Preferred Embodiments using the singular or plural number may also include the plural or singular number respectively. The word "or" in reference to a list of two or more items, covers all of the following interpretations of the word: any of the items in the list, all of the items in the list, and any combination of the items in the list.

The above-detailed description of embodiments of the disclosure is not intended to be exhaustive or to limit the teachings to the precise form disclosed above. While specific embodiments of and examples for the disclosure are described above for illustrative purposes, various equivalent modifications are possible within the scope of the disclosure, as those skilled in the relevant art will recognize. Further, any specific numbers noted herein are only examples: alternative implementations may employ differing values, measurements or ranges.

Although the operations of any method(s) disclosed or described herein either explicitly or implicitly are shown and described in a particular order, the order of the operations of each method may be altered so that certain operations may be performed in an inverse order or so that certain operations may be performed, at least in part, concurrently with other operations. In another embodiment, instructions or sub-operations of distinct operations may be implemented in an intermittent and/or alternating manner.

The teachings of the disclosure provided herein can be applied to other systems, not necessarily the system described above. The elements and acts of the various embodiments described above can be combined to provide further embodiments. Any measurements or dimensions described or used herein are merely exemplary and not a limitation on the present invention. Other measurements or dimensions are within the scope of the invention.

Any patents and applications and other references noted above, including any that may be listed in accompanying filing papers, are incorporated herein by reference in their entirety. Aspects of the disclosure can be modified, if necessary, to employ the systems, functions, and concepts of the various references described above to provide yet further embodiments of the disclosure.

These and other changes can be made to the disclosure in light of the above Detailed Description of the Preferred Embodiments. While the above description describes certain embodiments of the disclosure, and describes the best mode contemplated, no matter how detailed the above appears in text, the teachings can be practiced in many ways. Details of the system may vary considerably in its implementation details, while still being encompassed by the subject matter disclosed herein. As noted above, particular terminology used when describing certain features or aspects of the disclosure should not be taken to imply that the terminology is being redefined herein to be restricted to any specific characteristics, features or aspects of the disclosure with which that terminology is associated. In general, the terms used in the following claims should not be construed to limit the disclosures to the specific embodiments disclosed in the specification unless the above Detailed Description of the Preferred Embodiments section explicitly defines such terms. Accordingly, the actual scope of the disclosure encompasses not only the disclosed embodiments, but also all equivalent ways of practicing or implementing the disclosure under the claims.

While certain aspects of the disclosure are presented below in certain claim forms, the inventors contemplate the various aspects of the disclosure in any number of claim forms. For example, while only one aspect of the disclosure is recited as a means-plus-function claim under 35 U.S.C. § 112, ¶6, other aspects may likewise be embodied as a means-plus-function claim, or in other forms, such as being embodied in a computer-readable medium. (Any claims intended to be treated under 35 U.S.C. § 112, ¶6 will include the words "means for"). Accordingly, the applicant reserves the right to add additional claims after filing the application to pursue such additional claim forms for other aspects of the disclosure.

Accordingly, although exemplary embodiments of the invention have been shown and described, it is to be understood that all the terms used herein are descriptive rather than limiting, and that many changes, modifications, and substitutions may be made by one having ordinary skill in the art without departing from the spirit and scope of the invention.

What is claimed is:

1. A vaginal dilator assembly comprising:

a cylindrical main body portion that includes an axial portion, an offset portion and a lumen defined therein, wherein the main body portion includes a top surface, a bottom surface, a first side surface, a second side surface, a proximal end and a distal end, wherein the lumen extends from the axial portion to the offset portion, wherein the axial portion defines a first axis and the offset portion defines a second axis, and wherein the second axis is not co-axial with the first axis, wherein the cylindrical main body portion is an elongate body that is dimensioned for insertion into the vaginal canal, the distal end of the main body portion comprising a closed, rounded end, and the main body portion having an outer surface sized to dilate the vaginal canal upon insertion, and a rod disposed in the lumen, wherein the rod comprises a material that is more rigid than a material of the main body portion.

2. The vaginal dilator assembly of claim 1 wherein a vibration recess having a vibration surface is defined in the proximal end of the main body portion, whereby a vibration device can be placed into the vibration recess and against the vibration surface to transmit vibrations through the vaginal dilator assembly.

3. The vaginal dilator assembly of claim 2 wherein the rod is configured to transmit the vibrations from the proximal end of the main body portion to the distal end of the main body portion.

4. The vaginal dilator assembly of claim 2 further comprising a vibration device that includes a convex portion.

5. The vaginal dilator assembly of claim 2 further comprising a vibration device that includes a convex portion.

6. The vaginal dilator assembly of claim 1 wherein the main body portion comprises a silicone, and wherein the rod comprises a nylon.

7. The vaginal dilator assembly of claim 1 wherein a series of depth indicating numbers are arranged axially along the top surface of the main body portion.

8. The vaginal dilator assembly of claim 1 wherein the lumen is enclosed within the main body portion.

9. The vaginal dilator assembly of claim 1 wherein the main body portion includes an offset end portion defined between the distal end and the rod.

10. The vaginal dilator assembly of claim 1 wherein the second axis is not parallel with the first axis.

11. The vaginal dilator assembly of claim 1 wherein the offset portion is positioned toward the distal end and is flexible to avoid a pelvic bone during insertion.

12. A vaginal dilator assembly comprising:

a cylindrical main body portion that includes an axial portion, an offset portion and a lumen defined therein, wherein the main body portion includes a top surface, a bottom surface, a first side surface, a second side surface, a proximal end and a distal end, wherein the lumen extends from the axial portion to the offset portion, wherein the axial portion defines a first axis and the offset portion defines a second axis, wherein the second axis is not co-axial with the first axis, wherein a vibration recess having a vibration surface is defined in the proximal end of the main body portion, whereby a vibration device can be placed into the vibration recess and against the vibration surface to transmit vibrations through the vaginal dilator assembly, and a rod disposed in the lumen, wherein the rod comprises a material that is more rigid than a material of the main body portion.

13. The vaginal dilator assembly of claim 12 wherein the rod is configured to transmit the vibrations from the proximal end of the main body portion to the distal end of the main body portion.

14. The vaginal dilator assembly of claim 13 wherein the main body portion comprises a silicone, and wherein the rod comprises a nylon.

15. A method of using a vaginal dilator assembly, the method comprising the steps of:

obtaining the vaginal dilator assembly, wherein the vaginal dilator assembly includes a cylindrical main body portion and a rod disposed in a lumen defined in the main body portion, wherein the main body portion includes an axial portion, an offset portion and a lumen defined therein, wherein the main body portion includes a top surface, a bottom surface, a first side surface, a second side surface, a proximal end and a distal end, wherein the lumen extends from the axial portion to the offset portion, wherein the axial portion defines a first axis and the offset portion defines a second axis, wherein the second axis is not co-axial with the first axis, wherein the rod comprises a material that is more rigid than a material of the main body portion, wherein a vibration recess having a vibration surface is defined in the proximal end of the vaginal dilator assembly, obtaining a vibration device having a convex portion, inserting the vaginal dilator assembly into a vaginal canal, placing the convex portion of the vibration device in the vibration recess and against the vibration surface, and transmitting vibrations through the vaginal dilator assembly and to the vaginal canal.

* * * * *